(12) United States Patent
Lowe

(10) Patent No.: US 7,197,177 B2
(45) Date of Patent: Mar. 27, 2007

(54) AUTOMATED LAMINATE INSPECTION METHOD

(76) Inventor: Elvin P. Lowe, 476 Flaming Gorge Pines, Dutch John, UT (US) 84023

( * ) Notice: Subject to any disclaimer, the term of this patent is extended or adjusted under 35 U.S.C. 154(b) by 803 days.

(21) Appl. No.: 10/652,764

(22) Filed: Aug. 29, 2003

(65) Prior Publication Data

US 2005/0047643 A1   Mar. 3, 2005

(51) Int. Cl.
*G06K 9/00* (2006.01)
(52) U.S. Cl. ............... 382/141; 264/241; 264/258; 156/64; 156/264; 428/113; 428/218; 382/143
(58) Field of Classification Search ............... 382/141, 382/143; 428/110, 113, 218, 903, 212, 913, 428/220, 408, 120, 373, 118, 660, 332, 457, 428/102, 902, 174, 316.6; 264/29.5, 29.7, 264/241, 258, 29.6, 324; 156/64, 183, 182, 156/221, 222, 256, 264, 307.7; 442/411, 442/327, 409, 247, 346, 364, 414, 334; 423/447.1, 423/445 R; 416/229 R, 230; 162/164.1, 162/168.1, 100
See application file for complete search history.

(56) References Cited

U.S. PATENT DOCUMENTS

| | | | |
|---|---|---|---|
| 3,888,613 A * | 6/1975 | Fries et al. .................. 425/160 |
| 3,977,932 A * | 8/1976 | Fries et al. .................. 156/212 |
| 4,139,591 A * | 2/1979 | Jurisich ....................... 264/257 |
| 4,201,823 A * | 5/1980 | Russell ........................ 428/194 |
| 4,950,355 A * | 8/1990 | Klose .......................... 156/204 |
| 5,317,387 A * | 5/1994 | Van Hengel et al. ....... 356/625 |
| 5,954,898 A * | 9/1999 | McKague et al. ............. 156/64 |
| 6,028,910 A * | 2/2000 | Kirchner et al. ............... 378/22 |
| 6,064,031 A * | 5/2000 | Talwar .................. 219/121.64 |
| 6,187,411 B1 * | 2/2001 | Palmer ....................... 428/102 |
| 7,112,299 B2 * | 9/2006 | Merrick ..................... 264/510 |

* cited by examiner

*Primary Examiner*—Sheela Chawan
(74) *Attorney, Agent, or Firm*—Donald W. Meeker

(57) ABSTRACT

An optical scanner scans a piece support of know thickness holding a cross-section of laminate material such as fiber composite laminate, metal laminates, brazed parts, welded parts, sandwiched parts to determine layer thickness and layer properties such as fiber content, matrix content, density, void content, and other desired properties related to quality control for real time feedback to manufacturing and archiving for future reference. The electronic visual image from the scan depicts the number and quality of pixels in each layer. A programmable data processor uses the scan information and reference data to determine the physical properties and of the stacking order and the fiber orientation of a fiber reinforced laminate, and the thickness of each ply of metal and sandwich laminates as well as bonded, welded and brazed joints and for the determination of the thickness of each ply, of the stacking order and fiber orientation of a fiber reinforced laminate. The processor outputs real time data and a connected data storage memory archives the information for future reference.

14 Claims, 1 Drawing Sheet

AUTOMATED LAMINATE INSPECTION METHOD

BACKGROUND OF THE INVENTION

1. Field of the Invention

The present invention relates to a method and an apparatus for inspection of laminate material and in particular to the visual inspection by scanning for the characterization of laminate material, including fiber composite laminate material, metal laminates, brazed parts, welded parts, sandwich parts to determine layer thickness and layer properties such as fiber content, matrix content, density, void content, and other desired properties related to quality control for real time feedback to manufacturing and archiving for future reference, in particular for the determination of the thickness of each ply, and of the physical properties and of the stacking order and the fiber orientation of a fiber reinforced laminate, and the thickness of each ply of metal and sandwich laminates as well as bonded, welded and brazed joints.

2. Description of the Prior Art

Laminated materials, due to the ability to tailor and optimize the electrical, thermal and mechanical properties of the end product, have and are accelerating in application to items extending from sporting goods to aviation products, aerospace and military items, electronic products, automotive parts, and construction components. For primary structural products for the above mentioned industries the ability of the designer to optimize a reinforcing fiber orientation in multi-layers or plies through the cross section allows achieving very high elected directional strength or stiffness to weight ratios.

Likewise, for components with stringent coefficient of thermal expansion requirements the orientation and ratio of reinforcement to matrix are critical for each individual layer or ply. In the electronics industry applications, such as radar cross section reduction, RF energy absorption, radomes and other electronics components, the precise ratios of reinforcement to matrix as well as layer or ply thickness control are required to achieve the required dielectric constant value or electrical performance.

Many of these applications utilize carbon, graphite, glass, ceramic, aramid, metal or other fibers in a matrix of resin (thermoset or thermoplastic), ceramic, metal or other materials. The reinforcing fibers are plied, layered or stacked in the defined sequence and orientation to achieve the required end product performance. To achieve the end product performance not only the fiber plied or stacked sequence and orientation must be precise but also the thickness and reinforcement to matrix ratio for each unique layer or ply must be precisely as defined at design and maintained during the manufacturing process. As the raw materials or pre-impregnated reinforcing fibers have a tolerance as to the amount of reinforcing fiber per unit area, as well as the amount of matrix material per unit area, the resulting layer or ply thickness and reinforcing fiber to matrix material ratio must be adjusted or controlled by the manufacturing process. Currently, quality control procedures utilize as fabricated product thickness and laboratory destructive testing of a specimen from the end product. This methodology does not verify the precise thickness or the reinforcing fiber to matrix material ratio for each layer or ply within the cross section of the laminated end product. Additionally, the time required to perform these test renders the results useless in real time control of the manufacturing process for end products. The number of layers or plies and the orientation of reinforcing fibers for each layer or ply are verified only by visual inspection during manufacturing. This history record is the stamp on a planning document indicating that the inspector visually verified the process. There is no physical evidence available for future evaluation. In some cases photomicrographs of a cross section for a specimen from the end product is generated by encapsulating the specimen, polishing a surface and producing a photograph with a camera mounted onto a microscope. This process is labor intensive and time consuming. The information availability lag from completion of the end product to the photograph is too long to be a valuable tool to the manufacturing process or real time quality efforts. Additionally, interpretation of the photograph is unstructured and requires considerable evaluation and operator experience to obtain precise results.

These same issues occur with end products constructed of laminated sheets of metal adhesive bonded, metal parts welded or brazed, structures of face skins separated by honeycomb, foam or other materials as well as bonded joints.

Other methods have been described and some utilized to evaluate the reinforcing fiber orientation including burning off the resin matrix and removing layer by layer for visual verification of reinforcing fiber orientation and layer or ply count. (U.S. Pat. No. 5,317,387) Ultrasonic inspection is a common methodology utilized in the industry. Ultrasonic inspection is known to define flaws including foreign materials, delaminations and very high void content areas; however, these ultrasonic methodologies do not address the thickness, reinforcing fiber content, matrix content of each unique layer or ply.

Again, it is noted that to assure the performance of the end product to the design criteria the thickness, reinforcing fiber orientation, reinforcing fiber content, matrix content must be precisely as defined in the design details and specifications for each unique layer or ply of the laminate.

U.S. Pat. No. 6,041,132, issued Mar. 21, 2000 to Isaacs, is for a method of computed tomographic inspection which uses a Euclidian reference ply model that has a corresponding Non-Euclidian ply model, which includes reference model plies to extract intensity data from Euclidian slice data (typically having a pixel format) derived from multiple slice X-ray scans using an X-ray scanning system such as the CT system. The multiple slice data is analyzed to determine intensity values for points corresponding to a subject ply of a corresponding reference model ply. The reference model may be a predetermined model such as a mathematically described CAD model file or based on such a CAD model. A preferred method of the present invention includes a transformation of the CAD model data to register the CAD model data to multiple slice data of a standardized object to generate the reference model. Intensity values preferably gray scale pixel values are assigned to points on the reference ply model from the slice data and displayed as a Non-Euclidian image on a monitor.

U.S. Pat. No. 5,317,387, issued May 31, 1994 to Van Hengel, provides a method for the non-destructive determination of the stacking order and the fiber orientation of a fiber reinforced composite laminate. The method comprises illuminating optically successively a series of spots of a cross sectional surface of the laminate under examination and detecting light radiated from the respective illuminated spots. An electrical output signal relative to the amount of light detected is provided and a characterization of the laminate indicative of the stacking order and fiber orientation is determined from the electrical output signal. An apparatus is provided for carrying out the method of the present invention.

U.S. Pat. No. 5,341,436, issued Aug. 23, 1994 to Scott, claims a real-time radioscopy system that produces an X-ray image of a sample of reinforced composite material or a manufactured part that has been molded from the reinforced composite material. By examining the statistics of the distribution of gray levels within the image, it is possible to measure the local and average reinforcing material content (loading) as well as how well the reinforcing material is distributed (the reinforcing material dispersion). The mean gray level is used to determine the local loading of the reinforcing material, which is measured as a function of position in the sample or part using this technique. In addition, an average value of the loading may be obtained. The standard deviation of the gray level image correlates with the quality of dispersion of the reinforcing material.

U.S. Pat. No. 6,041,020, issued Mar. 21, 2000 to Caron, provides the investigation, development and application of a laser-based ultrasonic inspection system for the problems of evaluating polymer/graphite composite materials. The use of lasers to generate and detect ultrasonic waveforms in materials provides a means to detect material properties remotely. The study consisted of three main aspects: 1) A confocal Fabry-Perot (CFP) based system has been devolved which uses light reflected from the CFP interferometer to derive the ultrasonic signal. This allows higher frequency components of the detected waveforms to be discerned when compared to a CFP-based system using light transmitted through the CFP interferometer. 2) Thermoelastic and ablative laser generation of acoustic pulses in polymer/graphite composite materials has been investigated. Thermoelastic generation of ultrasound occurs when thermal energy deposited by a pulsed laser creates a localized expansion in the material. Ablative generation of ultrasound results from the creation of a plasma above the surface when the laser pulse surpasses an intensity threshold. 3) A novel technique, designated Gas-Coupled Laser Acoustic Detection (GCLAD), has been realized, in which the ultrasonic wave is detected optically after it has been transmitted from sample to air. This technique has the advantage of being independent of surface reflectivity and optical smoothness, and has comparable sensitivity to the CFP-based system.

U.S. Pat. No. 5,963,660, issued Oct. 5, 1999 to Koontz, claims an electronic scanner that has a light source and a light sensitive head is connected via a cable to a computer. The scanner head detects reflected light from the surface of the composite material and generates an electronic representation of the surface. A conventional software driver interprets the scanner output to produce an electronic bit-mapped image. The electronic image is then displayed so gaps are readily visible. The electronic representation is also analyzed to determine the presence of laps and gaps, to measure gap widths, to measure the distance between points on the display, and to determine the percentage of the surface covered by fiber material. The electronic representation may also be stored for later analysis.

U.S. Pat. No. 6,028,910, issued Feb. 22, 2000 to Kirchner, concerns a laminographic apparatus and method for imaging individual layers of a multilayer structure, for example the individual layers of a composite, with capabilities for imaging in multiple dimensions or along arbitrary surfaces within the space of the structure. A source of radiation and an areal detector are moved relative to a test specimen positioned therebetween such that a magnified two dimensional image of the test specimen is obtained at the detector. A single translational pass of the test specimen through the source/detector combination provides sensitivity to patterns in the test specimen, which have small scale features lying in a direction parallel to the direction of the pass. An image with sensitivity to features in two perpendicular directions is obtained by taking passes in both directions; no mechanical registration between the perpendicular passes being required. To reconstruct a point along the pass, only local mechanical registration (over for example an inch or so) between the source, test specimen and detector is required for each pass; each point is reconstructed from a predetermined number of images taken over the short distance for which local mechanical registration was required. One or more surfaces of the test specimen may be reconstructed using digitized data of the images.

U.S. Pat. No. 5,562,788, issued Oct. 8, 1996 to Kitson, shows a method of and apparatus for detecting flaws on a composite surface laid-up by a fiber placement machine. The invention includes a vision imaging system mounted on the machine so that it has a field of view of the composite tows after they have been compacted by a compaction roller. In one embodiment, the visual imaging system includes a laser analog displacement sensor. The imaging system provides a computer analysis system with data regarding the location of the edges of the individual composite tows. The computer imaging system uses the tow edge location data to compute the location and size of gaps or overlaps between the tows or the presence of foreign material. This information is useful in quality control models to evaluate the manufacturing process or final part quality.

What is needed is a method and apparatus which can quantify, report and archive the data associated with the properties of each unique layer or ply such as but not limited to the reinforcing fiber type, matrix type, thickness, reinforcing fiber content, matrix content, density, void content, adhesive thickness, braze area thickness and area of migration for jointed materials in a structured, non-personnel interpreted, timely and non-labor intense manner consistent with real-time support to the manufacturing environment.

SUMMARY OF THE INVENTION

The principal object of the present invention is to provide a method to characterize a laminated material with which quantitative data of each unique layer or ply can be obtained in a relatively fast, non-personnel interpreted and easy manner.

Another object of this invention is to provide the characterization of each unique ply or layer in a manner that can be automated.

Yet another object of this invention is to provide a method and apparatus that produce characterization reports and archives data consistent with the time line useful to the manufacturing environment.

A further object of the present invention is to provide a technique that uses recent pixel technology, which comprises a visual imaging device taken from the list of visual imaging devices, which includes but not limited to a visual scanner, a digital camera, and video camera with or without additional magnifications devices.

In brief, the present invention provides a simple and inexpensive method for the determination of the physical properties, and archiving the data associated with those determinations, for laminated type materials. Physical properties to be inspected include, but are not limited to, those of fiber reinforced composite laminates such as ply thickness, fiber orientation, matrix content, reinforcement content, void content or metal laminates physical properties such as metallic layer thickness, adhesive thickness, braze alloy thickness, weld penetration.

The method involves the creation of an electronic image of a prepared cross section of the product (or of a very small specimen cut from the product) by means of a scanner or camera (digital or video) with or without the additional utilization of magnifying lenses. During the process of creating the electric image, the product or product specimen is supported in a holder which provides a reference to be utilized during the electronic processing of the image as a calibration standard for precise linear distance.

Once the electronic image is imported to an electronic processing program an operator may select manually the boundaries defining the materials of interest limits or select an automated process to define the physical limits of unique materials or layers or plies. The automated process evaluates an optimum number of pixels horizontally on the display screen to obtain a sufficiently stable color or grayscale value result and indexes to the next line of pixels repeating the process. Each horizontal line color or grayscale value result is graphed versus the vertical location of the horizontal line of pixels. Changes in the sufficiently stable color or grayscale value result will clearly identify the physical limits of unique materials or layer or plies.

By the use of the calibration standard from the product or product specimen holder, a precise dimensionally accurate definition for each unique material or layer of material defined by the operator or by the automated process can be derived. This information is then utilized with information selected by the operator from a database within the electronic processing program to calculate, report and archive data defining the physical properties of the product or product specimen. The properties can be as simple as each material or layer or ply thickness to more complex properties such as matrix content, reinforcement content, void content, density, intermingling zone between material layers, migration of weld, braze or adhesive into the joined materials.

Further evaluation of the electronic image and comparison with known characteristics of the reinforcement stored in a database can permit determination of the fiber orientation. This is accomplished by electronically imaging by scanner or camera (digital or video) with or without additional magnifying apparatus a properly prepared edge of the end product, or a specimen from the end product, and supporting that end product edge, or specimen edge, with the proper holder providing edge and dimensional references. That image is characterized by an electronic processing program to define the boundary of each unique ply or layer and with that information related to the dimensional references on the holder quantitative dimensional aspects of each ply or layer is defined. The electronic processing program then relates the layer or ply dimensional data to a data base defining such properties as reinforcing fiber content, matrix density, etc. for each unique layer or ply. All the properties data, materials identification and end product identification data along with the image is reported and archived. Additional information unique to each ply of layer such as void content, migration of material into other layers or plies, intermingling of layers or plies is determined. Information as to the orientation of the reinforcing fibers within each unique layer or ply is determined by comparison with known fiber dimensions and observed projected dimensions in the layer or ply.

Electronic imaging of the end product edge or specimen edge is accomplished with or without magnification in conjunction with the scanner or camera (digital or video). The preparation of the edge under examination and the frequency or type of light to illuminate the edge is selected to optimize the electronic image.

This type of method and apparatus is also used to evaluate scarfed edges of the end product, or specimen from the end product, to directly measure the reinforcing fiber orientation in each unique ply of layer. By applying this method to each unique layer or ply during the manufacturing phase of the end product, an electronic image of each unique layer or ply in the plane of that layer or ply can be generated for immediate evaluation by the electronic processing program to assure compliance of the reinforcing fiber orientation to the end product design and specification. These images can be combined to successfully evaluate, report and archive the data for the manufacturing process before final consolidation and cure of the matrix material. Following the final processing these data can be compared to the evaluation of the edge or scarfed edge to ascertain any shift of movement during cure.

An advantage of the present invention is that it works instantly to analyze samples.

Another advantage of the present invention is that it uses recent pixel technology in scanners and cameras.

An additional advantage of the present invention is that it may be used in an automated manufacturing process.

One more advantage of the present invention is that it provides a higher degree of accuracy in measurements compared to those done by personnel.

Yet another advantage is that the system is easy to set up.

A further advantage of the present invention is that it lowers the cost of manufacturing of fiber reinforced composite laminates.

BRIEF DESCRIPTION OF THE DRAWINGS

These and other details of my invention will be described in connection with the accompanying drawings, which are furnished only by way of illustration and not in limitation of the invention, and in which drawings.

BEST MODE FOR CARRYING OUT THE INVENTION

Figure 1:
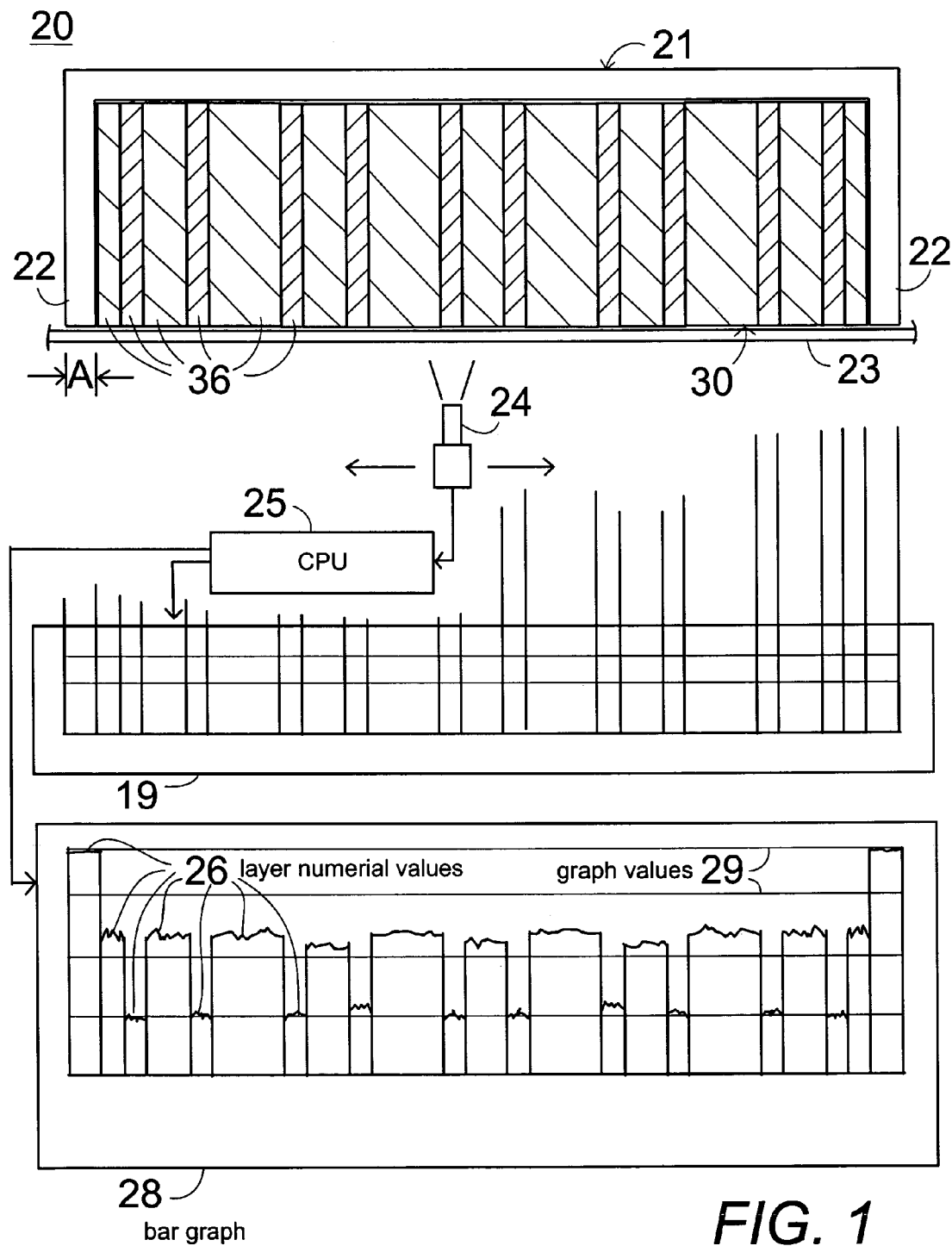
FIG. 1 illustrates a schematic view of the system for determining characteristics of laminate material.

In FIG. 1, a system 20 is shown for determining characteristics of laminate material 30, including fiber composite laminate material, metal laminates, brazed parts, welded parts, sandwich parts to determine layer thickness and layer properties such as fiber content, matrix content, density, void content, and other desired properties related to quality control for real time feedback to manufacturing and archiving for future reference, in particular for the determination of the thickness of each ply, and of the physical properties and of the stacking order and the fiber orientation of a fiber reinforced laminate, and the thickness of each ply of metal and sandwich laminates as well as bonded, welded and brazed joints. The system 20 comprises a holder 21 that is capable of supporting a sample piece of laminate material 30 so that an edge of the sample piece of laminate material 30 reveals a clearly visible view of the laminated layers 36 of the material 30 which may comprise fibers and binder material with the fibers oriented in a particular direction. The holder 21 has a sample piece support surface 22 of known thickness (A), which is visible adjacent to the edge of the sample piece of laminate material 30 showing the laminated layers 36 of the material 30.

The system 20 also comprises a visual scanning means 24 capable of viewing the edge of the piece of laminate material 30 and the sample piece support 22 of known thickness (A) and scanning an electronic image of the laminated layers 36 of the material 30 and the sample piece support 22. The electronic image comprises an array of pixels that have different visual characteristics dependent upon the content of each of the layers 36. The visual scanning means 24 comprises a visual imaging device taken from the list of visual imaging devices, which includes a visual scanner, a digital camera, or a video camera. A graph 19 of the number of pixels in each layer displayed horizontally on the graph to determine the thickness of each layer by comparing the number of pixels in the sample piece support 22 of known thickness A with the number of pixels in each layer 36.

The system 20 further comprises a programmable means 25, such as a CPU in a personal computer, for automatically receiving and analyzing the electronic image. The programmable means 25 is capable of differentiating between the different visual characteristics thereby determining the layer 36 configurations. The visual characteristic values 26 comprise gray scale values or color values, as shown in the bar graph 28 in FIG. 1.

The laminate material 30 may be formed by fibers bundled together in parallel arrays and combined together in layers 36. Each layer 36 has bundles of fibers stacked at different angles from each adjacent layer 36. The visual characteristics vary with the angle of the fibers so that the programmable means 25 is capable of receiving calibrated values of angles associated with the visual characteristics and comparing the visual characteristic values 26 with the calibrated values to determine the angle of the fibers in each of the layers 36. The programmable means 25 is also capable of receiving input information about the desired angles of the fibers in each of the layers 36 and further capable of comparing the visually determined angle with the information input about the desired angle. The programmable means 25 is capable of comparing the scanned information with information input about the desired content and thickness of each layer 36, and further capable of outputting the comparative information in real time. The comparative information is output for use in a quality system for manufacturing the laminate material 30.

In practice, laminated materials which may be those made of carbon fibers have fibers laid down in layers at different angles and bound together. It is very important that each layer of carbon fibers or other type of fibers being used is exactly the right thickness and the fibers are at the exact correct angle, so that the laminated material will have the desired characteristics of strength or heat resistance or other properties for the intended use. Each piece of the laminated material is checked to make sure is made correctly.

The method for determining the characteristics of laminate material 30 comprises a first step of securing a sample piece of laminate material 30 in a holder 21, which is capable of supporting the sample piece of laminate material 30 so that an edge of the sample piece of laminate material 30 reveals a clearly visible view of the laminated layers 36 of the material 30. The holder 21 has a sample piece support surface 22 of known thickness (A), which is visible adjacent to the edge of the sample piece of laminate material 30 showing the laminated layers 36 of the material 30.

The method for determining the characteristics of laminate material also comprises a second step of scanning the edge of the sample piece of laminate material 30 with a visual scanning means 24. The visual scanning means is capable of viewing the edge of the piece of laminate material 30 and the sample piece support 22 of known thickness (A) through a glass plate 23 and scanning an electronic image of the laminated layers 36 of the material 30 and the sample piece support 22. The electronic image comprises an array of pixels that may be counted to determine layer thickness compared with the number of pixels in the sample piece holder 22 of known thickness A and the pixels have different visual characteristics dependent upon the content and fiber orientation of each of the layers 36.

The method for determining the characteristics of laminate material 30 further comprises a third step of inputting the electronic visual image into a programmable means 25 for automatically receiving and analyzing the electronic image. The system 20 uses the programmable means 25 for differentiating between the different visual characteristics thereby determining the layer 36 configuration, counting the number of pixels 19 in a line across each of the different layers 36 and comparing the number of pixels 19 with the number of 19 in the sample piece support 22 of known thickness (A) thereby determining the thickness of each layer 36. The system 20 then compares the scanned information with information input about the desired content and thickness of each layer 36, and outputs the comparative information in real time. Comparing the visual characteristics comprises comparing gray scale or color values 26, as shown in the bar graph 28 in FIG. 1. The step of outputting the comparative information is designed for use in a quality system for manufacturing the laminate material 30.

The third step may also be used to determine angles of carbon fibers that are layered in the laminate 30. The laminate material 30 is formed by fibers bundled and bound together with a binder material in parallel arrays and combined together in fiber material layers 36. Each fiber material layer 36 has bundles of fibers stacked at different angles from each adjacent fiber material layer 36. The visual characteristics vary with the angle of the fibers so that the method further comprises using the programmable means 25 for receiving calibrated values of angles associated with the visual characteristic values 26 and comparing the visual characteristics with the calibrated values to determine the angle of the fibers in each of the layers 36. The method also comprises receiving input information about the desired angles of the fibers in each of the layers 36 and comparing the visually determined angle with the information input about the desired angle. If the layers 36 are not as thick as they are supposed to be or have fibers at different angles than what is required, that information is immediately made available to the manufacturing line. The manufacturing line can then alter the manufacturing process to correct the thickness or angles of the fibers for the layers 36 which are incorrect.

While the example illustrated referred to a fiber composite laminate, it is understood that the preceding description is given merely by way of illustration and not in limitation of the invention and that various modifications may be made thereto without departing from the spirit of the invention as claimed including the application to other laminate material, including metal laminates, brazed parts, welded parts, sandwich parts to determine layer thickness and layer properties such as fiber content, matrix content, density, void content, and other desired properties related to quality control for real time feedback to manufacturing and archiving for future reference, in particular for the determination of the thickness of each ply, and of the physical properties and of the stacking order and the fiber orientation of a fiber reinforced laminate, and the thickness of each ply of metal and sandwich laminates as well as bonded, welded and brazed joints.

What is claimed is:

1. A system for determining characteristics of laminate material, including fiber laminate material, metal laminates, brazed parts, welded parts, sandwich parts to determine layer thickness and layer properties such as fiber content, matrix content, density, void content, and other desired properties related to quality control, the system comprising:
   a holder capable of supporting a sample piece of laminate material so that an edge of the sample piece of laminate material reveals a clearly visible view of the laminated layers of the material, the holder having at least one sample piece support surface of known thickness visible adjacent to the edge of the sample piece of laminate material showing the laminated layers of the material;
   a visual scanning means capable of viewing the edge of the piece of laminate material and the at least one sample piece support of known thickness and scanning an electronic image of the laminated layers of the material and the sample piece support, the electronic image comprising an array of pixels having different visual characteristics dependent upon the content of each of the layers;
   a programmable means for automatically receiving and analyzing the electronic image, the programmable means being capable of differentiating between the different visual characteristics thereby determining the layer configuration, capable of counting the number of pixels in a line across each of the different layers and comparing the number of pixels with the number of pixels in the at least one sample piece support of known thickness thereby determining the thickness of each layer, capable of comparing the scanned information with information input about the desired content and thickness of each layer, and further capable of outputting the comparative information in real time.

2. The system of claim 1 wherein the comparative information is output for use in a quality system for manufacturing the laminate material.

3. The system of claim 1 wherein the visual characteristics comprise gray scale values.

4. The system of claim 1 wherein the visual characteristics comprise color values.

5. The system of claim 1 wherein the laminate material is formed by fibers bundled together in parallel arrays and combined together in layers with each layer having bundles of fibers stacked at different angles from each adjacent layer, and the visual characteristics vary with the angle of the fibers so that the programmable means is capable of receiving calibrated values of angles associated with the visual characteristics and capable of comparing the visual characteristics with the calibrated values to determine the angle of the fibers in each of the layers, and capable of receiving input information about the desired angles of the fibers in each of the layers and further capable of comparing the visually determined angle with the information input about the desired angle.

6. The system of claim 1 wherein the visual scanning means comprises a visual imaging device taken from the list of visual imaging devices including a visual scanner, a digital camera, and a video camera all with or without added magnifying devices.

7. The system of claim 1 further comprising a data storage means capable of storing information about the characteristics of the laminate material for archiving the information for future reference.

8. A method for determining characteristics of laminate material, including fiber laminate material, metal laminates, brazed parts, welded parts, sandwich parts to determine layer thickness and layer properties such as fiber content, matrix content, density, void content, and other desired properties related to quality control, the method comprising:
   a first step of securing a sample piece of laminate material in a holder capable of supporting the sample piece of laminate material so that an edge of the sample piece of laminate material reveals a clearly visible view of the laminated layers of the material, the holder having at least one sample piece support surface of known thickness visible adjacent to the edge of the sample piece of laminate material showing the laminated layers of the material;
   a second step of scanning the edge of the sample piece of laminate material with a visual scanning means capable of viewing the edge of the piece of laminate material and the at least one sample piece support of known thickness and scanning an electronic image of the laminated layers of the material and the sample piece support, the electronic image comprising an array of pixels having different visual characteristics dependent upon the content of each of the layers;
   a third step of inputting the electronic visual image into a programmable means for automatically receiving and analyzing the electronic image, and using the programmable means for differentiating between the different visual characteristics thereby determining the layer configuration, counting the number of pixels in a line across each of the different layers and comparing the number of pixels with the number of pixels in the at least one sample piece support of known thickness thereby determining the thickness of each layer, comparing the scanned information with information input about the desired content and thickness of each layer, and outputting the comparative information in real time.

9. The method of claim 8 further comprising the step of outputting the comparative information for use in a quality system for manufacturing the laminate material.

10. The method of claim 8 wherein comparing the visual characteristics comprises comparing gray scale values.

11. The method of claim 8 wherein comparing the visual characteristics comprises comparing color values.

12. The method of claim 8 wherein the laminate material is formed by fibers bundled together in parallel arrays and combined together in layers with each layer having bundles of fibers stacked at different angles from each adjacent layer, and the visual characteristics vary with the angle of the fibers so that the method further comprises using the programmable means for receiving calibrated values of angles associated with the visual characteristics and comparing the visual characteristics with the calibrated values to determine the angle of the fibers in each of the layers, and receiving input information about the desired angles of the fibers in each of the layers and comparing the visually determined angle with the information input about the desired angle.

13. The method of claim 8 wherein the second step comprises using a visual scanning means comprising a visual imaging device taken from the list of visual imaging devices including a visual scanner, a digital camera, and a video camera all with or without added magnifying devices.

14. The method of claim 8 further comprising storing information about the characteristics of the laminated material in a data storage means capable of storing information for archiving the information for future reference.

* * * * *